United States Patent [19]
Riccobono et al.

[11] Patent Number: 5,416,587
[45] Date of Patent: May 16, 1995

[54] INDEX INTERFEROMETRIC INSTRUMENT INCLUDING BOTH A BROAD BAND AND NARROW BAND SOURCE

[75] Inventors: Juanita R. Riccobono, Nashua; Jacque E. Ludman, Hollis, both of N.H.

[73] Assignee: Northeast Photosciences, Hollis, N.H.

[21] Appl. No.: 87,885

[22] Filed: Jul. 9, 1993

[51] Int. Cl.[6] .............................................. G01B 9/02
[52] U.S. Cl. .................................. 356/361; 356/357; 356/360
[58] Field of Search ............... 356/357, 359, 360, 361, 356/358, 349

[56] References Cited

U.S. PATENT DOCUMENTS 5,159,408 10/1992 Waldenmeir et al. ............... 356/357

OTHER PUBLICATIONS

Diana Tentori and Carlos Lopez, "High-Accuracy Critical Angle Refractometry," *Optical Engineering*, Mar. 1993, pp. 593–601. Shows that there are methods to improve the accuracy of refractive measurements that use prisms.

Diana Tentori, "High-Precision Refractometry by Hologram and Interferometry," *Optical Engineering* Apr. 1992, pp. 805–808. Explains a method for using interference patterns to measure the refractive index of an optical glass sample in the form a wedge by comparisons with a reference liquid.

Diana Tentori and Jesus Lerma, "Refractometry by Minimum Deviation: Accuracy Analysis," *Optical Engineering*, Feb. 1992, pp. 160–168. Analyzes the accuracy achieved when evaluating high refractive indices by minimum deviation deflectometry.

*Metricon Model 2010 Prism Computer* 1991, (advertisement) Describes a device utilizing a prism and a laser beam that can be directed at different angles to obtain an optical propagation mode that can be used to determine the index of refraction and thickness of thin film.

Roger Johnston and W. Kevin Grace, "Refractive Index Detector Using Zeeman Interfermetry", *Applied Optics*, 1 Nov. 1990, pp. 4720–4724. Discusses the theory and error analysis for an ultrasensitive refractive index detector using a Zeeman effect laser.

R. W. Ditchburn, *Light*, 1976, pp. 332–337. Describes measuring refractive index with interferometers.

Alan Werner, "Methods in High Precision Refractometry of Optical Glasses," *Applied Optics*, May 1968, pp. 837–844. Describes five refractive methods and an interferomtric method for measuring refractive indices of optical glasses.

H. G. Jerrard, "Sources of Error in Ellipsometry," *Proceeding of the Symposium on Recent Developments in Ellipsometry*, 1968, pp. 67–87. Describes sources of error in ellipsometry.

G. E. Fishter, "Refractometry," *Applied Optics and Optical Engineering* (Kingslake), 1967, pp. 363–383. Background material on refractometry.

O. S. Heavens, *Optical Properties of Thin Films*, 1965, pp. 4–5, 96–131. Explores various methods for measuring film thickness.

(List continued on next page.)

*Primary Examiner*—Samuel A. Turner
*Attorney, Agent, or Firm*—Adam Erlich

[57] ABSTRACT

The Index Interferometric Instrument is a highly accurate instrument which can be utilized to measure the index of refraction, the dispersion, and the index profile of materials. The instrument provides the data necessary to measure the index of refraction of materials to five significant figures. The index profile can be measured at any chosen wavelength without any sample preparation. The instrument utilizes a 10 nm to a 400 nm bandwidth light source and a light source with a bandwidth of less than 10 nm in combination with an interferometer. Each light source creates interference patterns from the sample and a reference mirror which can be used to accurately calculate the index of refraction of an entire sample at any given point on the sample.

10 Claims, 3 Drawing Sheets

OTHER PUBLICATIONS

Elio Passaglia, R. R. Stromberg, and J. Kruger eds., *Ellipsometry in the Measurement of Thin Films*, 1964, pp. 1, 34–39. Describes the optics of absorbing film on metal.

Leroy Tilton, "Testing and Accurate Use of Abbe-Type Refractometers," *Journal of the Optical Society of America*, Jul. 1942, pp. 371–381. Background material on refractometer.

H. W. Straat and J. W. Forrest, "The Accuracy Requirements in Fifth Place Refractometry," Jun. 1939, pp. 240–247. Background material on refractometers.

Jacques Ludman and Juanita Riccobono, "Index Interferometer," 20–1 Jul. 1992, Reprint from *Optical Information Processing Systems and Architecture*, pp. 258–264. This is the inventors article. The present application was filed less than one year after the publication and the presentation that this publication was based upon. Therefore, the publication is no considered prior art.

INDEX INTERFEROMETRIC INSTRUMENT INCLUDING BOTH A BROAD BAND AND NARROW BAND SOURCE

BACKGROUND OF THE INVENTION

This invention relates generally to a highly accurate index interferometric instrument, and more particularly, to one that utilizes a first light source with a bandwidth ranging from approximately 10 nm to 400 nm and a second light source with a bandwidth of less than 10 nm, such as a laser, to create interference patterns, which can be used to accurately calculate the index of refraction of an entire sample at any given point.

The index of refraction of a material and its homogeneity give important information as to the nature of the material, its impurities, its stoichiometry and the uniformity of the impurity distribution. A number of techniques have been used to measure the index of refraction and its variation throughout a material sample. One method is to dip samples into index-matching liquids. However, this method is not very accurate nor does it give a good index profile. Another method requires the construction of triangular prisms of the material, which wastes material and loses information because of index variation along the beam path.

A conventional interferometer can be used to measure the index of refraction of thin materials with poor accuracy, but is ineffective in measuring a material sample with a thickness in excess of 10 microns. In such an interferometer a single laser beam is divided, with one part of the beam being directed towards a reference mirror and the other part of the beam being directed towards a sample, the sample being mounted to a mounting mirror. When the light reflected back from the sample and the reference mirror are recombined three interference patterns can be created. They represent the reflection of the laser light from the front of the sample, the reflection of the light from the back of the sample, and the reflection of the light from the mounting mirror. In addition to these three interference patterns a number of interference fringes are also created, which are almost indistinguishable from the three interference patterns.

If the sample is very thin, one can use such an interferometer to determine the thickness of the sample and determine the optical pathlength of the sample, which together can be used to calculate the index of refraction. The thickness of the sample can be determined by counting the number of interference fringes or fraction of fringes between the interference pattern created by the reflection from the front surface of the sample and the pattern created by the reflection from the mounting mirror. The optical pathlength of the sample can be determined by counting the number of fringes between the pattern created by the reflection from the front surface of the sample and the pattern created by the back surface of the sample. The index of refraction can be calculated by utilizing the formula $n=(p/t)+1$, where $n$=the index of refraction, $p$=the optical pathlength of the sample, and $t$=the thickness of the sample. However, for a sample with a thickness of much greater than one fringe, it is very difficult to locate interference patterns and differentiate these patterns from interference fringes.

If the interferometer utilizes a white light source instead of a laser, localized, and easily distinguishable interference patterns can be created. However, if the sample is relatively thick, the white light source will be dispersed as it passes through the sample and will not be able to create an interference pattern from the back of the sample. Also, the white light source does not have interference fringes continuously from the front surface reflection to the back surface reflection. Thus, the distance between each of the patterns can not be measured for a thick sample utilizing white light.

It would be highly desirable if an instrument were available which could be used to accurately measure the index of refraction of an entire sample.

SUMMARY OF THE INVENTION

This present invention overcomes the problems associated with previous interferometers by providing an instrument which can be used to determine the index of refraction of a wide variety of samples. By utilizing a 10 nm–400 nm bandwidth light source in combination with an interferometer it is possible to create interference patterns from the front and back surfaces of the sample. In addition, by using a light source with a bandwidth of less than 10 nm, such as a laser, interference fringes can be created to provide a reference which makes it possible to accurately calculate the index of refraction and dispersion effect of a relatively thick sample at any given point on the sample.

The instrument of the present invention measures the index of refraction of a sample having a wide variety of thicknesses by utilizing a less than 10 nm bandwidth light source, such as a laser, and a 10 nm–400 nm bandwidth light source in combination with an interferometer. The 10 nm–400 nm bandwidth light source creates three distinct and filtered light interference patterns representing the reflection of light from the front of the sample, the back of the sample, and the mounting mirror. These interference patterns can be viewed through the eyepiece of the interferometer. The 10 nm–400 nm bandwidth light source can penetrate the sample and create an interference pattern from the back of the sample. Also, the 10 nm–400 nm bandwidth light source creates distinguishable, localized filtered light interference patterns.

A light source with a bandwidth of less than 10 nm creates interference fringes which can be used to measure the distance between the interference patterns from the 10–400 nm light source. These measurements of the distance between the filtered light interference patterns can then be used to calculate the index of refraction of the sample. Also, the sample can be manipulated within the interferometer, which would make it possible to measure the index of refraction of different portions of the sample.

It is therefore an object of this invention to provide an interferometric instrument having a means of illuminating a sample with two narrow band light sources, one that has a bandwidth of between 10 and 400 nm and another light source of less than 10 nm. The sample is illuminated while moveably affixed within an interferometer in order to create interference fringes and patterns. These fringes and patterns allow for an accurate calculation of the index of refraction of the sample, regardless of varying sample thickness.

It is another object of the invention to provide an interferometric instrument having a means for manipulating and accurately illuminating various portions of the sample with the light sources. This would allow for the measurement of the index profile for the entire sample, regardless of changes in thickness throughout the sample.

For a better understanding of the present invention, together with other and further objects thereof, reference is now made to the following description taken in conjunction with the accompanying drawings, and its scope will be detailed in the appended claims.

DETAILED DESCRIPTION OF THE PREFERRED EMBODIMENT

Figure 1:
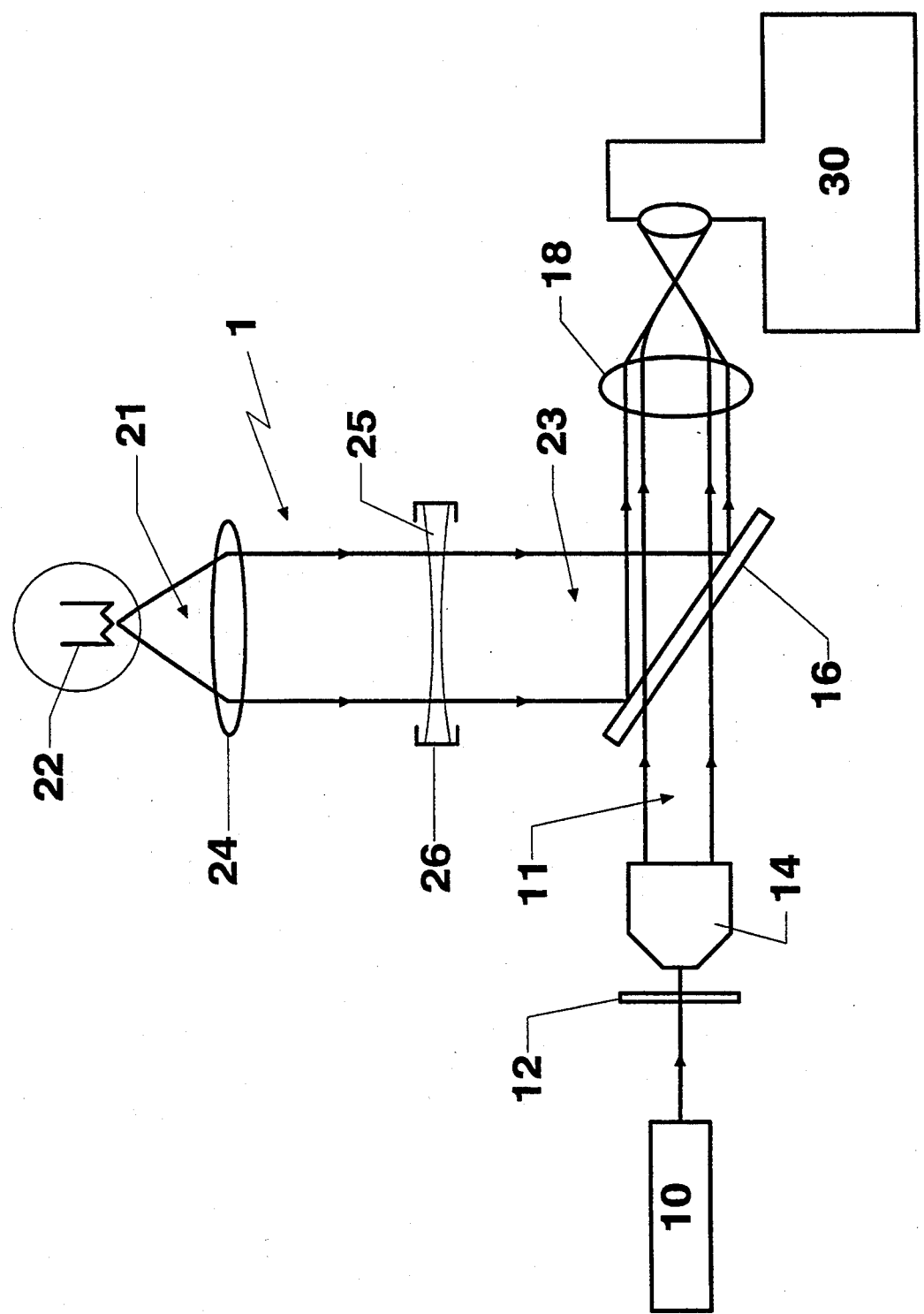
FIG. 1 of the drawings is a schematic representation of the index interferometric instrument of this invention.

Reference is now made to FIG I of the drawings, which illustrates the index interferometric instrument 1 of the present invention. The index interferometric instrument 1 has the capability of utilizing both a filtered light source and a non-filtered laser light source to illuminate a sample in order to create filtered light interference patterns from the filtered light source and reference fringes from the laser. By counting the reference fringes between the filtered light interference patterns either manually or by an automated fringe counter an accurate measure of the thickness and pathlength of the sample can be obtained. Utilizing the formula $n=(p/t)+1$, where $n=$ the index of refraction, $p=$ the optical pathlength of the sample, and $t=$ the thickness of the sample, the index of refraction of the sample can be calculated. Thus by utilizing the interferometric instrument of this invention a very accurate measure of the index of refraction of a relatively thick sample can be obtained in the manner described in detail hereinbelow.

More specifically, the index interferometric instrument 1 is composed of a laser 10, which transmits laser light 11 that passes through a diffuser 12 and a beam expander 14 to degrade the spatial coherence of the light 11 from laser 10. This degradation procedure reduces the speckle effect. The laser light 11 leaves beam expander 14, passes through conventional beam splitter 16 and then through collector lens 18. Collector 18 concentrates and directs the laser light 11 into interferometer 30, the operation of which is set forth in detail below.

As shown in FIG. 1, the light source 22 projects a beam of light 21 that passes through a conventional collimator 24 and then through a variable bandwidth filter 25 preferably of about 70 nm. The filter 25 is fitted into a filter slot 26. The filtered light 23 is directed by the beam splitter 16 towards the collector 18, which concentrates and directs the filtered light 23 into interferometer 30. It is important to recognize that in the present invention laser light source 10 has a bandwidth of less than 10 nm, while light source 22 has a bandwidth which can vary between 10 nm–400 nm.

Figure 2:
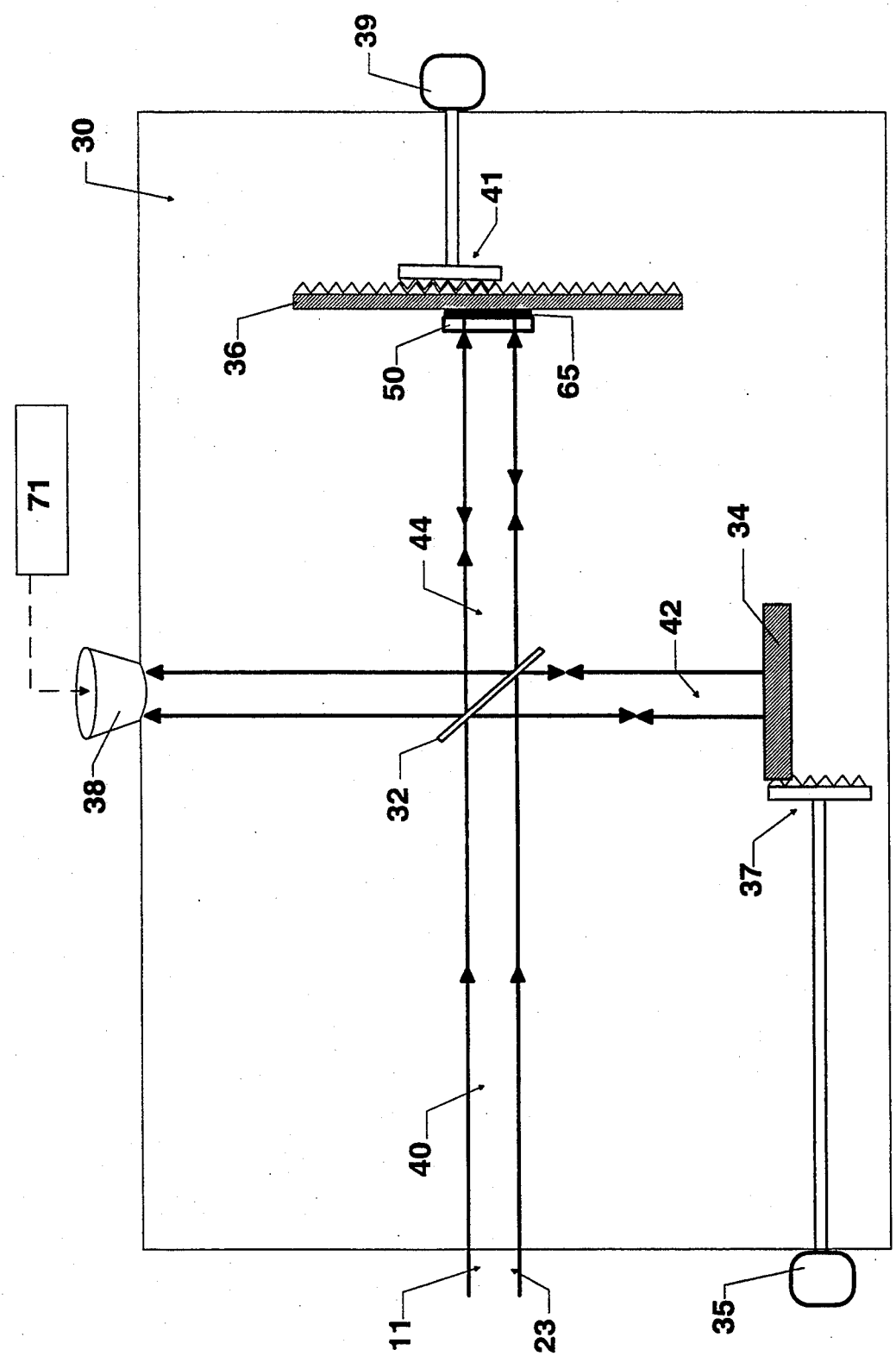
FIG. 2 of the drawings is a schematic representation of the interferometer used within the index interferometric instrument of this invention.

Reference is now made to FIG. 2 which schematically illustrates interferometer 30 of interferometric instrument 1. Interferometer 30 is made up of conventional beam splitter 32, reference mirror 34, mounting mirror 36, eyepiece 38, knob 35, gearing system 37, knob 39, and gearing system 41.

As shown in FIG. 2, laser light 11 or filter light 23 form light beam 40 which enters interferometer 30. Beam 40 is split into beam 42 and beam 44 by conventional beam splitter 32. Beam 42 is directed at reference mirror 34 and beam 44 is directed at sample 50, which is mounted to mounting mirror 36.

The sample 50 is mounted to mounting mirror 36 with an index matching liquid 65. The index matching liquid 65 cohesively bonds sample 50 to the mounting mirror 36 and fills the gaps between sample 50 and the mounting mirror 36, which are caused by the roughness of sample 50.

Beam 44 is reflected from the front surface of sample 50, the back surface of sample 50, and the mounting mirror 36. A portion of the reflected light from beam 44 is directed by beam splitter 32 toward an eyepiece 38. The eyepiece 38 may be replaced by an automated fringe counter (not shown) if desired. Beam 42 is reflected from reference mirror 34 and passes through beam splitter 32 toward eyepiece 38. The reflected light from beam 42 and beam are recombined in the eyepiece 38.

Figure 4:
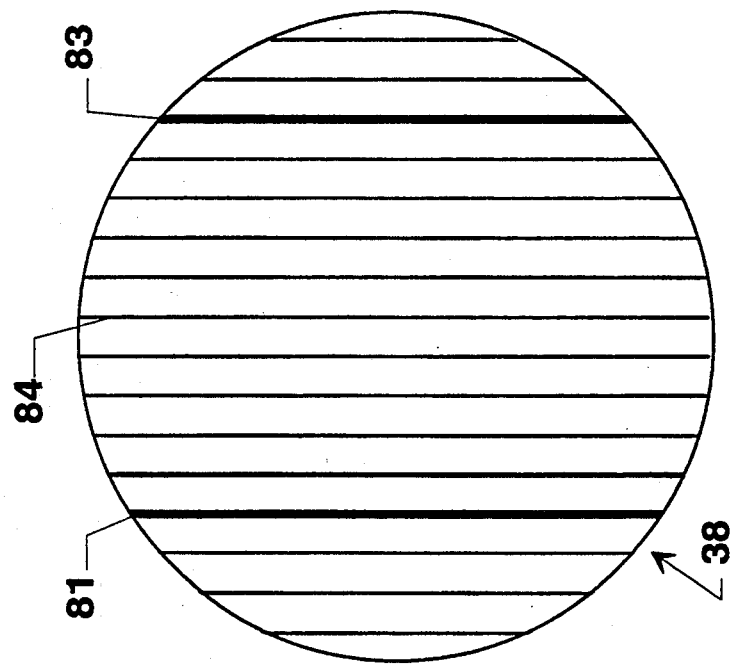
FIG. 3 and FIG. 4 of the drawings are pictorial representations of the interference patterns and reference fringes produced by the index interferometric instrument of this invention.
Figure 3:
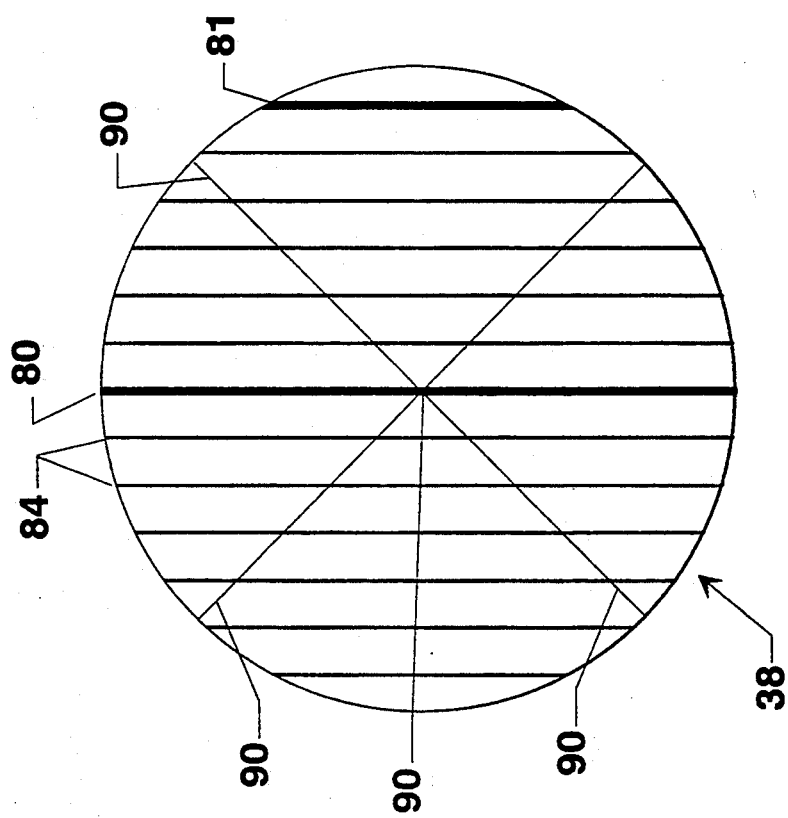

As shown in FIG. 2 and more particularly in FIG. 3 and FIG. 4, the filtered light 23 being reflected by the front surface of the sample 50, the back surface of sample 50, and the mounting mirror 36 can create three filtered light interference patterns 80, 81, 83, which can be seen using the eyepiece 38. The laser light 11 creates reference fringes 84, which can be seen through eyepiece 38 However, in order to see all three filtered light interference patterns 80, 81, 83 created by the different sections of sample 50 and mounting mirror 36, it is necessary to move reference mirror 34 closer to or further away from beam splitter 32. Knob 35 is connected to gearing system 37, which controls the motion of the reference mirror 34.

As shown in FIG. 3 and described below, the filtered light interference patterns 80, 81, 83 and reference fringes 84 can determine the thickness of the sample and the optical pathlength of the sample, which can be utilized to calculate the index of refraction of sample 50. The thickness of sample 50 can be determined by counting the number of reference fringes 84 or fraction of fringes between the filtered light interference patterns 81, created by the reflection from the mounting mirror 36, and the filtered light interference pattern 81, created by the reflection from the mounting mirror 36. The optical pathlength of the sample can be determined by counting the number of reference fringes 84 between the filtered light interference pattern 80, created by the reflection from the front surface of the sample 50, and the filtered light interference pattern 83, created by the back surface of the sample 50. The index of refraction can be calculated by utilizing the formula $n=(p/t)+1$, where $n=$ the index of refraction, $p=$ the optical pathlength of the sample, and $t=$ the thickness of the sample. This calculation can be performed manually or with an automated fringe counter 71. The index of refraction with respect to different wavelengths of light can be determined by changing filter 25 to the desired wavelength. Furthermore, positioning knob 39, which is connected to the gearing system 41 controls the motion of the mounting mirror 36, which alters which part of sample 50 is being illuminated by beam 44 and can be utilized to obtain the index profile of sample 50.

During the process of counting the number of reference fringes 84 between the filtered light interference patterns 80, 81, 83 it is necessary to alternately turn off and on the laser 10 and the light source 22. The location of an interference pattern 80 should be marked with crosshairs 90 inside eyepiece 38, while laser 10 is off and light source 22 is on. Then laser 10 should be turned on and light source 22 should be turned off. This prevents the light from light source 22 from interfering with the light from laser 10 and allows for an accurate count of interference fringes. This procedure should also be repeated for determining the number of reference fringes 84 between interference patterns 80, 81, 83.

Although this invention has been described with reference to particular embodiments, it will be understood that this invention is also capable of further and other embodiments within the spirit and scope of the appended claims.

We claim:

1. An index interferometric instrument comprising:
    a first light source having a bandwidth between 10 nm and 400 nm;
    a second light source having a bandwidth of less than 10 nm;
    a means for directing light from said first light source and said
    second light sources into an interferometer;
    said interferometer having a mounting mirror, a means for splitting
    a beam, and a reference mirror;
    a sample is mounted to said mounting mirror;
    light from said first light source and said second light source are split by said splitting means to illuminate said sample and said reference mirror; and
    light reflected from said sample, said mounting mirror, and said reference mirror is recombined and displayed through an optical output means.

2. An index interferometric instrument as defined in claim 1 further comprising: a means for preventing light from said first light source from
    illuminating said sample while light from said second light source is illuminating said sample and;
    a means for preventing light from said second light source from illuminating said sample while light from said first light source is illuminating said sample.

3. An index interferometric instrument as defined in claim 1 further comprising:
    a means for counting interference fringes which are displayed from said interferometer through said optical output means.

4. An index interferometric instrument as defined in claim 2 further comprising:
    a means for counting interference fringes which are displayed from said interferometer through said optical output means.

5. An index interferometric instrument as defined in claim 1 further comprising:
    a means for moving said reference mirror.

6. An index interferometric instrument as defined in claim 1 further comprising:
    a means for moving said mounting mirror.

7. An index interferometric instrument as defined in claim 1 further comprising:
    an eyepiece as said optical output means.

8. An index interferometric instrument as defined in claim 1 further comprising:
    a white light source and a filter as said first light source.

9. An index interferometric instrument as defined in claim 1 further comprising:
    a laser as said second light source.

10. An index interferometric instrument as defined in claim 1 further comprising:
    an index matching liquid which is used to cohesively mount said sample to said mounting mirror.

* * * * *